(12) United States Patent
Sugise et al.

(10) Patent No.: US 6,861,563 B2
(45) Date of Patent: Mar. 1, 2005

(54) PROCESS FOR PREPARATION OF CYCLODODECANONE

(75) Inventors: Ryoji Sugise, Ube (JP); Shuji Tanaka, Ube (JP); Takashi Doi, Ube (JP); Masayuki Nishio, Ube (JP); Sadao Niida, Ube (JP); Tsunao Matsuura, Ube (JP)

(73) Assignees: Ube Industries, Ltd. (JP); EMS-Chemie AG (CH)

( * ) Notice: Subject to any disclaimer, the term of this patent is extended or adjusted under 35 U.S.C. 154(b) by 0 days.

(21) Appl. No.: 10/486,735

(22) PCT Filed: Aug. 9, 2002

(86) PCT No.: PCT/JP02/08198

§ 371 (c)(1),
(2), (4) Date: Feb. 13, 2004

(87) PCT Pub. No.: WO03/016251

PCT Pub. Date: Feb. 27, 2003

(65) Prior Publication Data

US 2004/0181096 A1 Sep. 16, 2004

(30) Foreign Application Priority Data

Aug. 16, 2001 (JP) ........................................ 2001-247264

(51) Int. Cl.⁷ .............................................. C07C 45/67
(52) U.S. Cl. ....................... 568/341; 568/347; 568/348; 568/375
(58) Field of Search ................................ 568/341, 347, 568/348, 375

(56) References Cited

U.S. PATENT DOCUMENTS 4,885,397 A * 12/1989 Bueschken .................. 568/341
6,204,416 B1 * 3/2001 Liedloff ....................... 568/361
6,335,472 B1 * 1/2002 Matsuzaki et al. ........... 568/338
6,388,140 B2 * 5/2002 Sugise et al. ................ 568/341
6,417,404 B1 * 7/2002 Sugise et al. ................ 568/338
6,515,185 B1 * 2/2003 Kuroda et al. ............... 568/338

FOREIGN PATENT DOCUMENTS

| DE | 3601 380 A1 | 7/1987 |
|---|---|---|
| DE | 37 44094 A1 | 7/1989 |
| JP | 2001-39909 A | 2/2001 |
| JP | 2001-64224 A | 3/2002 |
| SU | 407874 | 12/1973 |

OTHER PUBLICATIONS

*Zh. Org. Khim*, 26(7), 1497–1500 (1990) [Document in Russian].

* cited by examiner

*Primary Examiner*—Johann Richter
*Assistant Examiner*—Sikarl A. Witherspoon
(74) *Attorney, Agent, or Firm*—Piper Rudnick LLP

(57) ABSTRACT

In the process for producing a cyclododecanone by isomerizing an epoxycyclododecane-containing starting material in the presence of an isomerization reaction catalyst containing lithium bromide and/or lithium iodide, in order to perform the reaction with high efficiency (high reaction rate) and high selectivity and stably produce a high-purity cyclododecanone in industry while maintaining a high-level reaction rate, the epoxycyclododecane-containing starting material is produced by contacting an epoxycyclododecadiene with hydrogen in the presence of a hydrogen-reduction catalyst and has a content of the hydroxyl group-containing cyclododecane compounds contained in the epoxycyclododecane-containing starting material controlled to 5 mol % or less.

5 Claims, No Drawings

PROCESS FOR PREPARATION OF CYCLODODECANONE

TECHNICAL FIELD

The present invention relates to a process for producing a high-purity cyclododecanone by isomerizing an epoxycyclododecane in the presence of a catalyst containing lithium bromide and/or lithium iodide. The cyclododecanone is a compound useful as a starting material of laurolactam, dodecanedioic acid, dodecane diol and the like.

BACKGROUND ART

The process for producing cyclododecanones by isomerizing an epoxycyclododecane in the presence of a lithium halide catalyst is known from several reports.

For example, German Patent DE3744094 discloses a technique where an epoxycyclododecane is isomerized by using N-methylpyrrolidone or N,N'-dimethylethyleneurea as a solvent and using lithium chloride as a catalyst and thereby a cyclododecanone is obtained in a yield of 94%.

Also, German Patent DE3601380 discloses a technique where 1,2-epoxycyclododeca-5,9-diene is isomerized in the presence of sodium iodide in a polyethylene glycol solvent (NaI: 3 wt %, 195° C., 9 hours) and thereby cyclododeca-3,7-dien-1-one is produced in a yield of 98.7%.

In either one of these methods, a polar solvent is used and therefore, a step for recovering or decomposing the solvent must be added, but this causes a problem of increase in the production cost. Furthermore, in these methods, the isomerization rate is decreased due to dilution effect or solvation effect of the solvent and this causes a problem that, for example, the reaction apparatus is large. Thus, these methods are not favored with an industrially high efficiency.

USSR Patent SU407874 discloses a technique of isomerizing an epoxycyclododecane by using no solvent and using anhydrous LiBr as the catalyst. In Examples of this patent, the reaction is performed by using 4 wt % of LiBr at a reaction temperature of 120 to 130° C. for a reaction time of 18 hours or by using 3.3 wt % of LiBr at a reaction temperature of 200° C. for a reaction time of 3 hours and thereby, the cyclododecanone is obtained in a yield of 100% or 83.3%, respectively. In the former Example, the reaction time is long and in the later Example, the yield is low. Thus, the methods are not practical.

In this USSR method, it may be considered to enhance the reaction rate by increasing the catalyst concentration or elevating the reaction temperature. However, in the former Example, the solubility of the catalyst comprising LiBr is already saturated at that reaction temperature and therefore, the catalyst concentration cannot be increased. In the latter Example, the reaction temperature is elevated so as to enhance the reaction rate, but in this case, a side reaction proceeds and the yield of the objective compound greatly decreases.

Furthermore, Zh. Org. Khim, 26(7), 1497–1500 (1990) discloses that when an isomerization reaction of an epoxycyclododecane is performed by using no solvent and using lithium bromide as the catalyst under the conditions of 2.3 mol of LiBr, 150° C. and 10 hours, the cyclododecanone is obtained in a yield of 96.6%, and when the reaction is performed by using lithium iodide as the catalyst under the conditions of 1.5 mol % of LiI, 150° C. and 5 hours, the cyclododecanone is obtained in a yield of 91.2%. However, also in the methods of this publication, it is feared that a fairly long reaction time is necessary to achieve a conversion close to 100% of epoxycyclododecane.

As described above, conventional production processes of cyclododecanones through isomerization of epoxycyclododecanes have those problems and a production process of a cyclododecanone, which can be practiced in an industrial scale with high efficiency and high selectivity, is not yet found out.

One problem encountered in industrially practicing the process for producing a cyclododecanone by isomerizing an epoxycyclododecane is the difficult separation of the cyclododecanone as the objective compound from the epoxycyclododecane used as the starting material. More specifically, the boiling point of the epoxycyclododecane and the boiling point of the cyclododecanone as an isomerization reaction product thereof are close to each other and, therefore, when unreacted epoxycyclododecane remains in the reaction system, the separation and recovery of this compound from the cyclododecanone by distillation is very difficult. Furthermore, these two compounds analogize with each other in the physical properties (for example, crystallinity and solubility) and therefore, the separation and recovery of two compounds by crystallization or extraction is also difficult. Accordingly, when unreacted epoxycyclododecane remains in the reaction system, a high-purity cyclododecanone can be hardly recovered. At the same time, from the above-described reasons, the unreacted epoxycyclododecane can be hardly recovered and re-used by an ordinarily employed technique but a special recovery technique is necessary and this inevitably causes an increase in the production cost of the objective compound. Therefore, in order to stably produce a high-purity cyclododecanone in industry, it is necessary to constantly achieve a nearly 100% conversion of the epoxycyclododecane. For realizing this in industry, the reaction rate must be maintained in a high level.

However, as described above, conventional techniques fail to provide a level high enough for industrial practice. Furthermore, if the reaction temperature is elevated so as to enhance the reaction rate, a side reaction readily takes place to produce a high-boiling-point material or the like and this causes a problem of reduction in the selectivity to cyclododecanone. In order to solve this problem, it may be considered to elevate the catalyst concentration, but this is not practical because the solubility of catalyst is limited and furthermore, the catalyst cost increases.

The epoxycyclododecane used as a starting material in the process of the present invention can be industrially produced by subjecting a cyclododecatriene obtained through trimerization of butadiene to an appropriate combination of oxidation reaction and hydrogenation reaction. For example, an epoxycyclododecadiene obtained by epoxidizing a cyclododecatriene is subjected to reduction with hydrogen in the presence of a catalyst such as platinum, palladium or nickel, whereby the epoxycyclododecane can be obtained.

In the thus-obtained epoxycyclododecane, hydroxyl group-containing cyclododecane compounds such as cyclododecanol are contained as impurities, but the effect of such impurities on the isomerization of epoxycyclododecane has been heretofore not studied. That is, a technique capable of efficiently producing a cyclododecanone from a starting material containing such impurities, with high selectivity in an industrial scale is not known at present. Here, the epoxycyclododecane and the hydroxyl group-containing cyclododecane compound such as cyclododecanol can be separated by a general industrial method such as distillation.

DISCLOSURE OF THE INVENTION

An object of the present invention is to provide a process for producing a cyclododecanone through an isomerization reaction of an epoxycyclododecane by using lithium bromide and/or lithium iodide as the catalyst, where the isomerization reaction can be performed with high efficiency (a high reaction rate) and high selectivity and a high-purity cyclododecanone can be stably produced, in the industry, while maintaining the high-level reaction rate.

As a result of intensive investigations to solve those problems, the present inventors have found that when an epoxycyclododecane-containing starting material is produced by hydrogen-reduction of an epoxycyclododecadiene, hydroxyl group-containing cyclododecane compounds such as cyclododecanol contained as impurities extremely decrease the reaction rate in the isomerization of the epoxycyclododecane. As described above, the epoxycyclododecane used as a starting material and the cyclododecanone produced as the objective compound can be hardly separated by a normal industrial technique. Accordingly, if the reaction rate is low and a part of the starting material epoxycyclododecane remains unreacted within a practical reaction time, a high-purity cyclododecanone is difficult to obtain.

The above-described object can be attained by the process of the present invention. That is, the process of the present invention for producing a cyclododecanone comprises a step of isomerizing a starting material mainly comprising an epoxycyclododecane in the presence of a catalyst containing at least one member selected from lithium bromide and lithium iodide to produce a cyclododecanone, wherein the epoxycyclododecane-containing starting material is one prepared by contacting an epoxycyclododecadiene with hydrogen in the presence of a hydrogen reduction catalyst and having a total content of the hydroxyl group-containing cyclododecane compounds contained in the starting material controlled to 5 mol % or less.

In the production process of a cyclododecanone of the present invention, the isomerization reaction is preferably carried out in an inert gas atmosphere.

In the production process of a cyclododecanone of the present invention, the catalyst for the isomerization reaction preferably contains lithium iodide.

In the production process of a cyclododecanone of the present invention, the hydrogen reduction catalyst for producing the epoxycyclododecane-containing starting material is preferably a platinum-supported catalyst.

In the production process of a cyclododecanone of the present invention, the epoxycyclododecane-containing starting material prepared by the catalytic reaction with hydrogen is preferably distilled to control the total content of the hydroxyl group-containing cyclododecane compounds to 5 mol % or less.

BEST MODE FOR CARRYING OUT THE INVENTION

The present invention is described in detail below.

The epoxycyclododecane used as a starting material compound in the process of the present invention is a saturated cyclic hydrocarbon containing 1 epoxy group and having 12 carbon atoms. This epoxycyclododecane has isomers with respect to the epoxy group and all isomers are included in the epoxycyclododecane for use in the process of the present invention. That is, in the process of the present invention, the epoxycyclododecane may have a single steric chemical structure or may be a mixture of two or more isomers.

The epoxycyclododecane is produced by reducing an epoxycyclododecadiene with hydrogen in the presence of a metal catalyst. Examples of the metal component of the catalyst include platinum, palladium and nickel. Among these, platinum is preferably used as the metal component of the catalyst, because if a catalyst containing palladium or nickel as the metal component is used, a large amount of a hydroxyl group-containing cyclododecane compound such as cyclododecanol is produced as a by-product. However, even when a platinum catalyst is used, the amount of the by-produced hydroxyl group-containing cyclododecane compound such as cyclododecanol sometimes increases due to the change in the reaction conditions and the like. Therefore, the reaction conditions must be appropriately established and maintained.

Specifically, the production of an epoxycyclododecane through hydrogen-reduction is performed by the following method.

The catalyst containing platinum as the metal component is preferably a solid catalyst where a compound containing a platinum element is supported on an inactive support, more preferably a powder catalyst, still more preferably a powder catalyst having an average particle size of a few $\mu$m to tens of $\mu$m. The inactive support can be selected from active carbon, alumina, silica, silica alumina, zeolite, spinel and the like, but is preferably active carbon, alumina, silica or silica alumina, more preferably active carbon. The amount of the platinum element supported on the inactive support is preferably from 0.1 to 10 mass %, more preferably from 0.2 to 8% by mass, based on the mass of the inactive support. The platinum element in the catalyst is supported on the surface or in the inside, preferably both on the surface and in the inside, of the inactive support.

The amount of the platinum catalyst used in the hydrogen-reduction reaction of the epoxycyclododecadiene is, as the platinum element, preferably 0.0005 times by mol or less, more preferably from 0.000001 to 0.0004 times by mol, based on the molar amount of the epoxycyclododecadiene in the starting material.

In the hydrogen-reduction reaction of the epoxycyclododecadiene, a solvent is not necessarily required but in the case of using an organic solvent as the solvent, examples of the solvent which can be used include hydrocarbons such as n-hexane, n-heptane, n-tetradecane and cyclohexane, ethers such as tetrahydrofuran and dioxane, alcohols such as methanol, ethanol, tert-butanol and tert-amyl alcohol, and esters such as ethyl acetate and butyl acetate. These organic solvents may be used individually or as a mixture of two or more thereof. The amount of the organic solvent used is preferably from 0 to 200 times by weight based on the weight of the starting material 1,2-epoxy-5,9-cyclododecadiene used.

The hydrogenation for the double bond of the epoxycyclododecadiene is performed in a hydrogen gas atmosphere at a reaction hydrogen pressure of 0.8 to 9 MPa by mixing the epoxycyclododecadiene and the platinum catalyst.

At this time, the reaction temperature is not particularly limited but is preferably higher than 50° C., more preferably from 70 to 200° C., still more preferably from 70 to 150° C.

In this method of producing an epoxycyclododecane from an epoxycyclododecadiene, hydroxyl group-containing cyclododecane compounds such as hydroxycyclododecadiene, hydroxycyclododecene and hydroxycyclododecane (cyclododecanol) are by-produced as impurities.

Depending on the case, a compound having two hydroxyl groups, such as cyclododecane diol, is produced.

In the process of the present invention, the total content of hydroxyl group-containing cyclododecane compounds contained as impurities in the epoxycyclododecane-containing starting material is controlled to 5 mol % or less, preferably 3 mol % or less.

That is, the epoxycyclododecane-containing starting material must be controlled such that the total amount of various hydroxyl group-containing cyclododecane compounds contained becomes 5 mol % or less.

If the content of the hydroxyl group-containing cyclododecane compound exceeds 5 mol %, the isomerization rate decreases and the selectivity to the objective cyclododecanone also decreases.

For controlling the total content to the above-described range, the total amount of hydroxyl group-containing cyclododecane compounds produced is controlled to 5 mol % or less in the step of producing the epoxycyclododecane, or the epoxycyclododecane-containing starting material is subjected to a purification step such as distillation before the starting material is used for the isomerization reaction in the process of the present invention.

In order to control the total amount of hydroxyl group-containing cyclododecane compounds contained in the produced epoxy cyclododecane to 5 mol % or less in the step of producing the epoxycyclododecane, the inactive support used for the platinum-supported catalyst is preferably alumina, silica or active carbon, more preferably active carbon. The content of the platinum element in the platinum-supported catalyst is preferably 0.0005 times by mol or less, more preferably from 0.000001 to 0.0004 times by mol, based on the amount of the epoxycyclododecadiene ("ECD") used. Also, the temperature in the hydrogenation reaction is preferably controlled to 50° C. or more, more preferably from 70 to 200° C. Furthermore, the hydrogen pressure in the hydrogenation reaction is preferably controlled to 0.8 to 9 MPa, more preferably from 1 to 8 MPa.

In the present invention, for controlling the total content of hydroxyl group-containing cyclododecane compounds in the epoxycyclododecane-containing starting material to be used for the isomerization reaction to 5 mol % or less, it is effective to previously distill the epoxycyclododecane-containing starting material. The method for this distillation treatment is not particularly limited. Examples of the distilling apparatus which can be used include a normal Sneader-type distillator, a packed tower-type distillator, a perforated plate-type distillator and a bubble cap tower-type distillator.

The distillation conditions are not particularly limited and the distillation can be usually performed under atmospheric pressure or reduced pressure (for example, from 0.1 to 40 kPa). The distillation temperature is set according to the distillation pressure, but is preferably 200° C. or less, more preferably from 90 to 180° C.

The catalyst used for the isomerization reaction in the process of the present invention is lithium bromide and/or lithium iodide. A special pre-treatment or the like before use as a catalyst is not necessary and lithium bromide and/or lithium iodide usually available on the market can be used as it is. Specifically, the catalyst for isomerization reaction is a compound containing one or more member selected from anhydrous lithium bromide, lithium bromide monohydrate, lithium bromide dihydrate, lithium bromide trihydrate, anhydrous lithium iodide, lithium iodide monohydrate, lithium iodide dihydrate, lithium iodide trihydrate and the like. This lithium compound may be used for the isomerization reaction in the solid state but may be used for the reaction in the state of being dissolved in an epoxycyclododecane or a cyclododecanone or in the state of an aqueous solution. Also, these compounds may be used as a mixture of two or more thereof.

The amount used of the catalyst for isomerization reaction is not particularly limited and is set by taking account of reaction conditions and the like, such as solubility in a solvent, but the amount used is preferably from 0.01 to 20 mol %, more preferably from 0.1 to 5 mol %, per mol of the epoxycyclododecane in the starting material. If the amount of the catalyst used is less than 0.01 mol %, the necessary reaction time is prolonged and this may be disadvantageous in industry, whereas if the amount of the catalyst used exceeds 20 mol %, the catalyst cost may excessively increase.

The gas atmosphere for use in the isomerization reaction of the present invention is not particularly limited but an inert gas is preferably used. Examples of the inert gas used include a helium gas, a neon gas, an argon gas, a hydrogen gas, a nitrogen gas, a carbon monoxide gas, a methane gas and an ethylene gas. Among these, a nitrogen gas and an argon gas are preferred. One of these inert gases may be used or a mixture of two or more thereof may be used.

In the process of the present invention, the reaction temperature at the isomerization reaction is preferably from 100 to 350° C., more preferably from 120 to 300° C., still more preferably from 150 to 250° C., yet still more preferably from 160 to 240° C.

If the reaction temperature is less than 100° C., the reaction rate is low and this may be industrially improper, whereas if the reaction temperature exceeds 350° C., the amount of impurities produced may increase.

In the process of the present invention, the reaction pressure at the isomerization reaction is not particularly limited and the reaction may be performed under pressure, atmospheric pressure or reduced pressure.

In the process of the present invention, the reaction time at the isomerization reaction varies depending on the amount of the catalyst used and the reaction temperature, but a reaction time of 10 hours or less is usually sufficient.

In the process of the present invention, the reaction style at the isomerization reaction is not limited and either a continuous system or a batch system may be used.

In the process of the present invention, the construction material of the reactor used for the isomerization reaction is not particularly limited and, for example, a glass-made or stainless steel-made reactor can be used.

In the process of the present invention, the isomerization reaction of the epoxycyclododecane is usually performed without a solvent and in this case, the epoxycyclododecane or the produced cyclododecanone plays the role of a solvent. However, use of a non-polar solvent is not inhibited.

Examples of the non-polar solvent include cyclic hydrocarbons having from 6 to 12 carbon atoms and the amount of the non-polar solvent used preferably does not exceed the amount (mass) of the epoxycyclododecane used.

According to the process of the present invention, the conversion of the starting material epoxycyclododecane can be maintained at nearly 100% and unreacted epoxycyclododecane is scarcely contained, so that the produced cyclododecanone can be easily purified by normal distillation. Incidentally, the cyclododecanone and the hydroxyl group-containing cyclododecane compound can be industrially separated by a purification method such as distillation.

EXAMPLES

The present invention will be further illustrated in detail below by the following examples and comparative examples.

In these examples and comparative examples, the starting material and the product were analyzed by a gas chromatograph equipped with a capillary column. In respective reaction conditions, a part (about 0.4 g) of the reaction solution was sampled at stages of 5 minutes, 10 minutes, 15 minutes, 20 minutes and 25 minutes after the initiation of reaction and analyzed, and the initial reaction rate constant K (min$^{-1}$) in respective conditions was calculated according to the reaction rate equation: d[CDON]/dt=K[ECD] (CDON: cyclododecanone, ECD: epoxycyclododecane).

The ECD conversion (=a ratio of the amount of ECD consumed in the reaction to the molar amount of ECD charged) and the CDON selectivity (=a ratio of the amount of CDON produced by the reaction to the amount of ECD consumed in the reaction) each was calculated on the molar basis.

The epoxycyclododecane used in each of Examples 1 to 6 and Comparative Examples 1 and 2 was obtained by reducing an epoxycyclododecadiene with hydrogen in the presence of a platinum catalyst (amount of platinum supported: 5 mass %) using active carbon as the support. At this time, the catalyst concentration was 0.01 mol % in terms of the platinum element based on the epoxycyclododecadiene, the hydrogen pressure was 5 MPa, the reaction temperature was 70° C. and the reaction time was 2 hours. The amount of cyclododecanol (CDOL) contained in the obtained epoxycyclododecane is shown in Table 1.

Example 1

In a glove box purged with a nitrogen atmosphere, 7.29 g of a mixture of the above-described epoxycyclododecane (cis:trans=35:65) and cyclododecanol was weighed into a 50 ml-volume glass-made Kjeldahl flask equipped with a thermometer, a magnetic rotor and a reflux condenser tube. The concentration of the cyclododecanol (CDOL) in this mixture was 0.37 mol %. Furthermore, 54 mg (0.047 mol/liter) of lithium iodide as the catalyst was weighed and placed into the flask and the obtained reaction system was heated by using an oil bath at a temperature of 200° C. and allowed to undergo an isomerization reaction under atmospheric pressure in a nitrogen atmosphere. The initial reaction rate constant K under these reaction conditions was calculated according to the reaction rate equation: d[CDON]/dt=K[ECD], and found to be 0.13 (min$^{-1}$).

The reaction was performed for 2 hours under the same conditions as above and the obtained reaction solution was cooled to room temperature and then analyzed by gas chromatography and, as a result, unreacted ECD was not detected and the selectivity to CDON was 99%.

Example 2

The reaction was performed by using the same conditions and operations as in Example 1 except that the concentration of cyclododecanol in the mixture of epoxycyclododecane (cis:trans=35:65) and cyclododecanol was changed to 0.70 mol %. The initial reaction rate constant was measured and, as a result, the initial reaction rate constant K under conditions of this Example was found to be 0.12 (min$^{-1}$).

The reaction was performed for 2 hours under the same conditions as above and the obtained reaction solution was cooled to room temperature and then analyzed by gas chromatography and, as a result, unreacted ECD was not detected and the selectivity to CDON was 99%.

Example 3

The reaction was performed by using the same conditions and operations as in Example 1 except that the concentration of cyclododecanol in the mixture of epoxycyclododecane (cis:trans=35:65) and cyclododecanol was changed to 1.0 mol %. The initial reaction rate constant was measured and, as a result, the initial reaction rate constant K under conditions of this Example was found to be 0.12 (min$^{-1}$).

The reaction was performed for 2 hours under the same conditions as above and the obtained reaction solution was cooled to room temperature and then analyzed by gas chromatography and, as a result, unreacted ECD was not detected and the selectivity to CDON was 99%.

Example 4

The reaction was performed by using the same conditions and operations as in Example 1 except that the concentration of cyclododecanol in the mixture of epoxycyclododecane (cis:trans=35:65) and cyclododecanol was changed to 2.0 mol %. The initial reaction rate constant was measured and, as a result, the initial reaction rate constant K under conditions of this Example was found to be 0.11 (min$^{-1}$).

The reaction was performed for 2 hours under the same conditions as above and the obtained reaction solution was cooled to room temperature and then analyzed by gas chromatography and, as a result, unreacted ECD was not detected and the selectivity to CDON was 99%.

Example 5

The reaction was performed by using the same conditions and operations as in Example 1 except that the concentration of cyclododecanol in the mixture of epoxycyclododecane (cis:trans=35:65) and cyclododecanol was changed to 3.0 mol %. The initial reaction rate constant was measured, as a result, the initial reaction rate constant K under conditions of this Example was found to be 0.11 (min$^{-1}$).

The reaction was performed for 2 hours under the same conditions as above and the obtained reaction solution was cooled to room temperature and then analyzed by gas chromatography and, as a result, unreacted ECD was not detected and the selectivity to CDON was 99%.

Example 6

The reaction was performed by using the same conditions and operations as in Example 1 except that the concentration of cyclododecanol in the mixture of epoxycyclododecane (cis:trans=35:65) and cyclododecanol was changed to 5.0 mol %. The initial reaction rate constant was measured, as a result, the initial reaction rate constant K under conditions of this Example was found to be 0.10 (min$^{-1}$).

The reaction was performed for 2 hours under the same conditions as above and the obtained reaction solution was cooled to room temperature and then analyzed by gas chromatography, as a result, the conversion of ECD was 99% and the selectivity to CDON was 99%.

Comparative Example 1

The reaction was performed by using the same conditions and operations as in Example 1 except that the concentration of cyclododecanol in the mixture of epoxycyclododecane (cis:trans=35:65) and cyclododecanol was changed to 7.0% on the molar basis. The initial reaction rate constant was measured and, as a result, the initial reaction rate constant K under conditions of this Comparative Example was found to be 0.08 (min$^{-1}$).

The reaction was performed for 2 hours under the same conditions as above and the obtained reaction solution was cooled to room temperature and then analyzed by gas chromatography and, as a result, the conversion of ECD was 97% and the selectivity to CDON was 98%.

Comparative Example 2

The reaction was performed by using the same conditions and operations as in Example 1 except that the concentration of cyclododecanol in the mixture of epoxycyclododecane (cis:trans=35:65) and cyclododecanol was changed to 20 mol %. The initial reaction rate constant was measured and, as a result, the initial reaction rate constant K under conditions of this Comparative Example was found to be 0.06 (min$^{-1}$).

The reaction was performed for 2 hours under the same conditions as above and the obtained reaction solution was cooled to room temperature and then analyzed by gas chromatography and, as a result, the conversion of ECD was 77% and the selectivity to CDON was 96%.

The results obtained in Examples 1 to 6 and Comparative Examples 1 and 2 are shown together in Table 1.

temperature, heated to a temperature of 70° C. Under the same pressure, the contents were heated with stirring until the hydrogen absorption did not occur. After the completion of reaction, the reaction solution was cooled to room temperature, the catalyst was removed by filtration and the resulting reaction solution was analyzed. The analysis of the reaction solution was performed by gas chromatography. As a result, 1,2-epoxy-5,9-cyclododecadiene was 100% consumed and epoxycyclododecane (hereinafter referred to as "ECD") was produced in a yield of 99.6 mol %. Also, as by-products, cyclododecanone (hereinafter referred to as "CDON") was produced in 0.04 mol %, cyclododecanol (hereinafter referred to as "CDOL") was produced in 0.20

TABLE 1

| | Reaction Conditions | | | Reaction Results | |
| | | | | Initial | Conversion | |
| | Concentration of LiI (mol/liter) | Reaction Temperature (° C.) | Concentration of CDOL (mol %) | Rate Constant K (min$^{-1}$) | of ECD (mol %) | Selectivity to CDON (mol %) |
|---|---|---|---|---|---|---|
| Example 1 | 0.047 | 200 | 0.37 | 0.13 | 100 | 99 |
| Example 2 | 0.047 | 200 | 0.70 | 0.12 | 100 | 99 |
| Example 3 | 0.047 | 200 | 1.0 | 0.12 | 100 | 99 |
| Example 4 | 0.047 | 200 | 2.0 | 0.11 | 100 | 99 |
| Example 5 | 0.047 | 200 | 3.0 | 0.11 | 100 | 99 |
| Example 6 | 0.047 | 200 | 5.0 | 0.10 | 99 | 99 |
| Comparative Example 1 | 0.047 | 200 | 7.0 | 0.08 | 97 | 98 |
| Comparative Example 2 | 0.047 | 200 | 20 | 0.06 | 77 | 96 |

[Note] of Table 1
(1) CDOL: cyclododecanol
(2) The conversion of ECD and the selectivity to CDON each was a value when the reaction was performed under the conditions of 200° C./2 hours.

As seen in Table 1, it was verified that when the CDOL content in the starting material is small, the rate constant in the isomerization reaction of ECD is high and the selectivity to the objective compound CDON is also high.

Example 7 (Synthesis of Epoxycyclododecane)

In an SUS-made autoclave having an inner volume of 100 ml and equipped with a stirrer, 20 g (0.112 mol) of 1,2-epoxy-5,9-cyclododecadiene and 0.08 g of a 5 mass % Pt/C catalyst (50% hydrous product, produced by N.E. Chemcat Corporation; 0.0102 mmol as platinum atom) were added and after pressurizing to 5 MPa with hydrogen at room mol % and cyclododecane (hereinafter referred to as "CDAN") was produced in 0.04 mol %.

Examples 8 to 12 and Comparative Examples 3 and 4

In each of Examples 8 to 12 and Comparative Examples 3 and 4, epoxycyclododecane was produced and analyzed in the same manner as in Example 7 except that the catalyst, the amount of catalyst, the reaction temperature and the reaction time were changed as shown in Table 2. The results are shown in Table 2.

TABLE 2

| | Catalyst | Amount of Catalyst (g) | Reaction Temperature (° C.) | Reaction Pressure (MPa) | Reaction Time (min) | Yield (mol %) | | | |
|---|---|---|---|---|---|---|---|---|---|
| | | | | | | ECD | CDON | CDOL | CDAN |
| Example 7 | 5 mass % Pt/C | 0.08 | 70 | 5 | 120 | 99.6 | 0.04 | 0.20 | 0.04 |
| Example 8 | 5 mass % Pt/C | 0.08 | 100 | 5 | 90 | 99.3 | 0.05 | 0.45 | 0.04 |
| Example 9 | 5 mass % Pt/C | 0.04 | 130 | 5 | 80 | 98.8 | 0.07 | 0.95 | 0.07 |
| Example 10 | 5 mass % Pt/C | 0.02 | 130 | 5 | 90 | 98.8 | 0.09 | 0.81 | 0.06 |
| Example 11 | 0.5 mass % Pt/alumina | 0.20 | 140 | 5 | 120 | 96.5 | 0.60 | 2.60 | 0.20 |
| Example 12 | 5 mass % Pt/C | 0.80 | 130 | 5 | 10 | 95.3 | 0.65 | 3.18 | 0.09 |
| Comparative Example 3 | 5 mass % Pt/C | 0.04 | 130 | 0.5 | 90 | 91.3 | 2.20 | 6.19 | 0.10 |
| Comparative Example 4 | 0.5 mass % Pd/C | 0.20 | 140 | 1 | 120 | 85.1 | 6.40 | 7.50 | 0.10 |

Example 13 (Synthesis of Cyclododecanone)

In a glove box purged with a nitrogen atmosphere, 7.29 g of a mixture of epoxycyclododecane (cis:trans=35:65) synthesized in Example 7 and cyclododecanol (0.20 mol %) was weighed into a 50 ml-volume glass-made Kjeldahl flask equipped with a thermometer, a magnetic rotor and a reflux condenser tube. Furthermore, 54 mg (0.047 mol/liter) of lithium iodide as the catalyst was weighed into the flask and the obtained reaction system was heated by using an oil bath at a temperature of 200° C. and allowed to undertake an isomerization reaction under atmospheric pressure in a nitrogen atmosphere. The initial reaction rate constant K under these reaction conditions was calculated according to the reaction rate formula: d[CDON]/dt=K[ECD] and found to be 0.13 (min$^{-1}$).

This reaction system was reacted for 2 hours under the same conditions as above and the obtained reaction solution was cooled to room temperature and then analyzed by gas chromatography, as a result, unreacted ECD was not detected and the selectivity to CDON was 99%.

Example 14

The reaction was performed by using the same conditions and operations as in Example 13 except for using a mixture of epoxycyclododecane (cis:trans=35:65) obtained in Example 8 and cyclododecanol (0.45 mol %). The initial reaction rate constant was measured, as a result, the initial reaction rate constant K under conditions of this Example was found to be 0.13 (min$^1$).

This reaction system was reacted for 2 hours under the same conditions as above and the obtained reaction solution was cooled to room temperature and then analyzed by gas chromatography, as a result, unreacted ECD was not detected and the selectivity to CDON was 99%.

Example 15

The reaction was performed by using the same conditions and operations as in Example 13 except for using a mixture of epoxycyclododecane (cis:trans=35:65) obtained in Example 9 and cyclododecanol (0.95 mol %). The initial reaction rate constant was measured and, as a result, the initial reaction rate constant K under conditions of this Example was found to be 0.12 (min$^{-1}$).

This reaction system was reacted for 2 hours under the same conditions as above and the obtained reaction solution was cooled to room temperature and then analyzed by gas chromatography and, as a result, unreacted ECD was not detected and the selectivity to CDON was 99%.

Example 16

The reaction was performed by using the same conditions and operations as in Example 13 except for using a mixture of epoxycyclododecane (cis:trans=35:65) obtained in Example 10 and cyclododecanol (0.81 mol %). The initial reaction rate constant was measured, as a result, the initial reaction rate constant K under conditions of this Example was found to be 0.12 (min$^{-1}$).

This reaction system was reacted for 2 hours under the same conditions as above and the obtained reaction solution was cooled to room temperature and then analyzed by gas chromatography and, as a result, unreacted ECD was not detected and the selectivity to CDON was 99%.

Example 17

The reaction was performed by using the same conditions and operations as in Example 13 except for using a mixture of epoxycyclododecane (cis:trans=35:65) obtained in Example 11 and cyclododecanol (2.60 mol %). The initial reaction rate constant was measured, as a result, the initial reaction rate constant K under conditions of this Example was found to be 0.11 (min$^{-1}$).

This reaction system was reacted for 2 hours under the same conditions as above and the obtained reaction solution was cooled to room temperature and then analyzed by gas chromatography and, as a result, unreacted ECD was not detected and the selectivity to CDON was 99%.

Example 18

The reaction was performed by using the same conditions and operations as in Example 13 except for using a mixture of epoxycyclododecane (cis:trans=35:65) obtained in Example 12 and cyclododecanol (3.18 mol %). The initial reaction rate constant was measured and, as a result, the initial reaction rate constant K under conditions of this Example was found to be 0.10 (min$^{-1}$).

This reaction system was reacted for 2 hours under the same conditions as above and the obtained reaction solution was cooled to room temperature and then analyzed by gas chromatography and, as a result, the conversion of ECD was 99% and the selectivity to CDON was 99%.

Comparative Example 5

The reaction was performed by using the same conditions and operations as in Example 13 except for using a mixture of epoxycyclododecane (cis:trans=35:65) obtained in Comparative Example 3 and cyclododecanol (6.19 mol %). The initial reaction rate constant was measured and, as a result, the initial reaction rate constant K under conditions of this Example was found to be 0.09 (min$^{-1}$).

This reaction system was reacted for 2 hours under the same conditions as above and the obtained reaction solution was cooled to room temperature and then analyzed by gas chromatography and, as a result, the conversion of ECD was 98% and the selectivity to CDON was 98%.

Comparative Example 6

The reaction was performed by using the same conditions and operations as in Example 13 except for using a mixture of epoxycyclododecane (cis:trans=35:65) obtained in Comparative Example 4 and cyclododecanol (7.50 mol %). The initial reaction rate constant was measured, as a result, the initial reaction rate constant K under conditions of this Example was found to be 0.07 (min$^{-1}$).

This reaction system was reacted for 2 hours under the same conditions as above and the obtained reaction solution was cooled to room temperature and then analyzed by gas chromatography, as a result, the conversion of ECD was 96% and the selectivity to CDON was 97%.

The analysis results in Examples 13 to 18 and Comparative Examples 5 and 6 are shown in Table 3.

TABLE 3

| | Reaction Conditions | | | Reaction Results | | |
|---|---|---|---|---|---|---|
| | | | | Initial | Conversion | |
| | Concentration of LiI (mol/liter) | Reaction Temperature (° C.) | Concentration of CDOL (mol %) | Rate Constant K (min⁻¹) | of ECD (mol %) | Selectivity to CDON (mol %) |
| Example 13 | 0.047 | 200 | 0.20 | 0.13 | 100 | 99 |
| Example 14 | 0.047 | 200 | 0.45 | 0.13 | 100 | 99 |
| Example 15 | 0.047 | 200 | 0.95 | 0.12 | 100 | 99 |
| Example 16 | 0.047 | 200 | 0.81 | 0.12 | 100 | 99 |
| Example 17 | 0.047 | 200 | 2.60 | 0.11 | 100 | 99 |
| Example 18 | 0.047 | 200 | 3.18 | 0.10 | 99 | 99 |
| Comparative Example 5 | 0.047 | 200 | 6.19 | 0.09 | 98 | 98 |
| Comparative Example 6 | 0.047 | 200 | 7.50 | 0.07 | 96 | 97 |

As seen from the analysis results in Table 3, it was verified that when the CDOL content in the starting material is small, the initial rate constant K value is large and the yield of CDON in the objective product is high.

Example 19

A mixed solution containing epoxycyclododecane (cis:trans=35:65) obtained in Comparative Example 3 and cyclododecanol (6.19 mol %) was purified by distillation at a distillation pressure of 0.93 kPa and a distillation temperature of 170° C.

As a result, the content of cyclododecanol contained in the epoxycyclododecane (cis:trans=35:65) was decreased to 0.82 mol %.

This purified starting material was used for the same isomerization reaction as in Example 13. The initial reaction rate constant K under the conditions of this Example was 0.12 (min⁻¹), the conversion of ECD was 100% and the selectivity to CDON was 99%.

INDUSTRIAL APPLICABILITY

According to the present invention, in the process of producing a cyclododecanone through an isomerization reaction of an epoxycyclododecane by using lithium bromide or lithium iodide, the reaction rate can be maintained at a high level and a high-purity cyclododecanone can be stably produced, in the industry, with high selectivity.

What is claimed is:

1. A process for producing a cyclododecanone, comprising a step of isomerizing a starting material comprising, as a principal component, an epoxycyclododecane, in the presence of a catalyst containing at least one member selected from lithium bromide and lithium iodide, to produce a cyclododecanone,
    wherein the epoxycyclododecane-containing starting material is one prepared by contacting an epoxycyclododecadiene with hydrogen in the presence of a hydrogen reduction catalyst and having a total content of the hydroxyl group-containing cyclododecane compounds contained in said starting material controlled to 5 mol % or less.

2. The production process of a cyclododecanone as claimed in claim 1, wherein the isomerization reaction is carried out in an inert gas atmosphere.

3. The production process of a cyclododecanone as claimed in claim 1 or 2, wherein the catalyst for the isomerization reaction contains lithium iodide.

4. The production process of a cyclododecanone as claimed in claim 1, wherein the hydrogen reduction catalyst for producing the epoxycyclododecane-containing starting material is a platinum-containing catalyst.

5. The production process of a cyclododecanone as claimed in claim 1, wherein the epoxycyclododecane-containing material prepared by the catalytic reaction with hydrogen is distilled to control the total content of the hydroxyl group-containing cyclododecane compounds to 5 mol % or less.

* * * * *